United States Patent [19]

Mitchell

[11] Patent Number: 4,912,262

[45] Date of Patent: Mar. 27, 1990

[54] CHEMICAL PROCESS

[75] Inventor: Glynn Mitchell, Iver Buckinghamshire, United Kingdom

[73] Assignee: Imperial Chemical Industries PLC, London, England

[21] Appl. No.: 164,963

[22] Filed: Mar. 7, 1988

[30] Foreign Application Priority Data

Mar. 19, 1987 [GB] United Kingdom ............... 8706557

[51] Int. Cl.$^4$ ............................................. C07C 45/45
[52] U.S. Cl. .................................... 568/312; 568/315; 568/316; 568/306; 560/51; 558/415; 564/315; 564/88
[58] Field of Search ............... 568/314, 312, 315, 316, 568/306; 560/51; 558/415; 564/315, 88

[56] References Cited

U.S. PATENT DOCUMENTS 4,695,673  9/1987  Heather et al. ..................... 568/314

FOREIGN PATENT DOCUMENTS 090262  10/1983  European Pat. Off. ............ 568/312

Primary Examiner—James H. Reamer
Attorney, Agent, or Firm—Cushman, Darby & Cushman

[57] ABSTRACT

According to the present invention there is provided process for preparing a compound of formula (I):

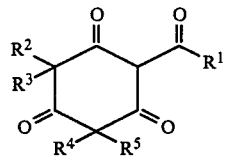

or a salt, acylate or sulphonate derivative thereof; wherein $R^1$ is an optionally substituted aryl group, $R^2$, $R^3$, $R^4$ and $R^5$ are selected from hydrogen, $C_{1-4}$ alkyl, $C_{1-4}$ alkanoyl or $-CO_2R^a$ wherein $R^a$ is $C_{1-4}$ alkyl or $R^2$ and $R^3$ or $R^4$ and $R^5$ together with the carbon atom to which they are attached form a $C_{3-6}$ cycloalkyl ring, provided that at least $R_2$ and $R^3$ or $R^4$ and $R^5$ are not both hydrogen and that not more than two of $R^2$, $R^3$, $R^4$ and $R^5$ are $C_{1-4}$ alkanoyl or $-CO_2R^a$; which process comprises reacting a compound of formula (II):

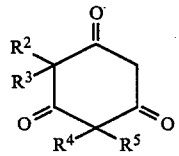

wherein $R^2$, $R^3$, $R^4$ and $R^5$ are as defined in relation to formula (I) with a compound of formula (III):

$R^1COCN$                (III)

wherein $R^1$ is as defined in relation to formula (I) in the presence of a base and a Lewis acid.

8 Claims, No Drawings

CHEMICAL PROCESS

The present invention relates to a process for the preparation of certain herbicidally active substituted cyclohexan-1,3,5-triones.

Copending European patent application No. EP-A-252298 describes and claims a series of 2-benzoyl-1,3,5-cyclohexanetriones, their use as herbicides and a route for their preparation. The applicants have now found an alternative route to these and some related compounds.

According to the present invention there is provided process for preparing a compound of formula (I):

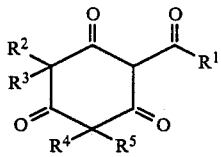
(I)

or a salt, acylate or sulphonate derivative thereof; wherein $R^1$ is an optionally substituted aryl group, $R^2$, $R^3$, $R^4$ and $R^5$ are selected from hydrogen, $C_{1-4}$ alkyl, $C_{1-4}$ alkanoyl or —$CO_2R^a$ wherein $R^a$ is $C_{1-4}$ alkyl or $R^2$ and $R^3$ or $R^4$ and $R^5$ together with the carbon atom to which they are attached form a $C_{3-6}$ cycloalkyl ring, provided that at least $R^2$ and $R^3$ or $R^4$ and $R^5$ are not both hydrogen and that not more than two of $R^2$, $R^3$, $R^4$ and $R^5$ are $C_{1-4}$ alkanoyl or —$CO_2R^a$; which process comprises reacting a compound of formula (II):

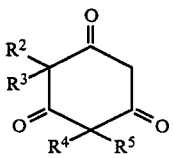
(II)

wherein $R^2$, $R^3$, $R^4$ and $R^5$ are as defined in relation to formula (I) with a compound of formula (III):

$R^1COCN$  (III)

wherein $R^1$ is as defined in relation to formula (I) in the presence of a base and a Lewis acid.

Suitable bases include both organic bases such as tertiary amines and inorganic bases such as alkali metal carbonates and phosphates. Suitable tertiary amines include trialkylamines such as triethylamine, trialkanolamines such as triethanolamine, and pyridine. Suitable inorganic bases include potassium carbonate and trisodium phosphate.

Suitable Lewis acids are zinc chloride and aluminium trichloride, preferably zinc chloride.

The reaction is carried out in an organic solvent such as acetonitrile or methylene chloride and at moderate temperatures of from −20° C. to +90° C.

Suitably both the zinc chloride and the base are present in a slight molar excess with respect to the compounds of formula (II) and (III).

Compound of formula (I) can exist in a number of tautomeric forms, for example:

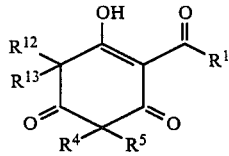

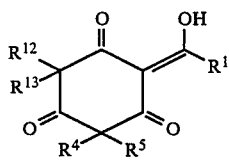

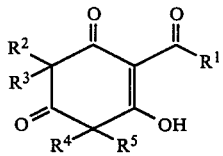

wherein $R^1$, $R^2$, $R^3$, $R^4$ and $R^5$ are as defined in relation to formula (I). When one or more of $R^2$, $R^3$, $R^4$ and $R^5$ are hydrogen, further tautomers exist.

Compounds of formulae (III) are either known compounds or they can be prepared from known compounds by conventional methods.

Compounds of formula (II) wherein $R^2$, $R^3$ are methyl and $R^4$ and $R^5$ are methyl or hydrogen and their preparation are described by Riedl and Risse (Justus Liebigs Annalen der Chemie, 1954, 585, 209).

Compounds of formula (II) wherein $R^2$, $R^3$, $R^4$ and $R^5$ are the same and are $C_{1-4}$ alkyl in particular methyl can be prepared by the following reaction Scheme A.

Scheme A

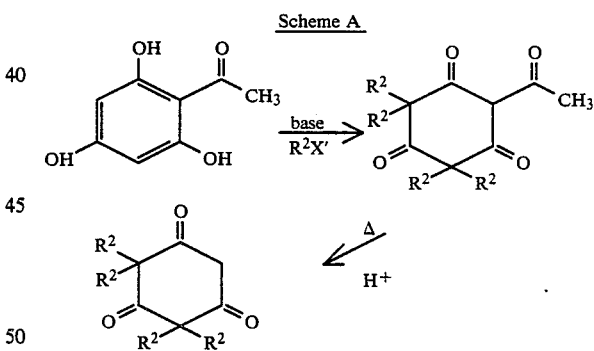

wherein X' is a leaving group such as halogen, in particular iodide. Suitable reaction conditions will be apparent by analogy with the above-mentioned publication. For example, one suitable base for use in the first step in Scheme A is sodium methoxide in methanol. A suitable acid for use in second step of Scheme A is an inorganic acid such as hydrochloric acid.

By adjusting the conditions in the first step of the process, it may be possible to obtain compounds of formula (II) wherein $R^4$ and/or $R^5$ are hydrogen.

Alternatively compounds of formula (II) can be prepared using the methods described by Murin et al (Chem. Ber. 1959, 92, 2033) or methods analogous thereto.

In this way compounds of formula (II) are prepared by cyclisation of a compound of formula (IV):

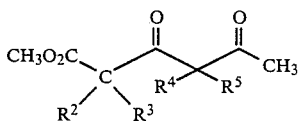

in the presence of a base such as sodium methoxide an organic solvent such as methanol. Compounds of formula (IV) can be prepared as outlined in Scheme B.

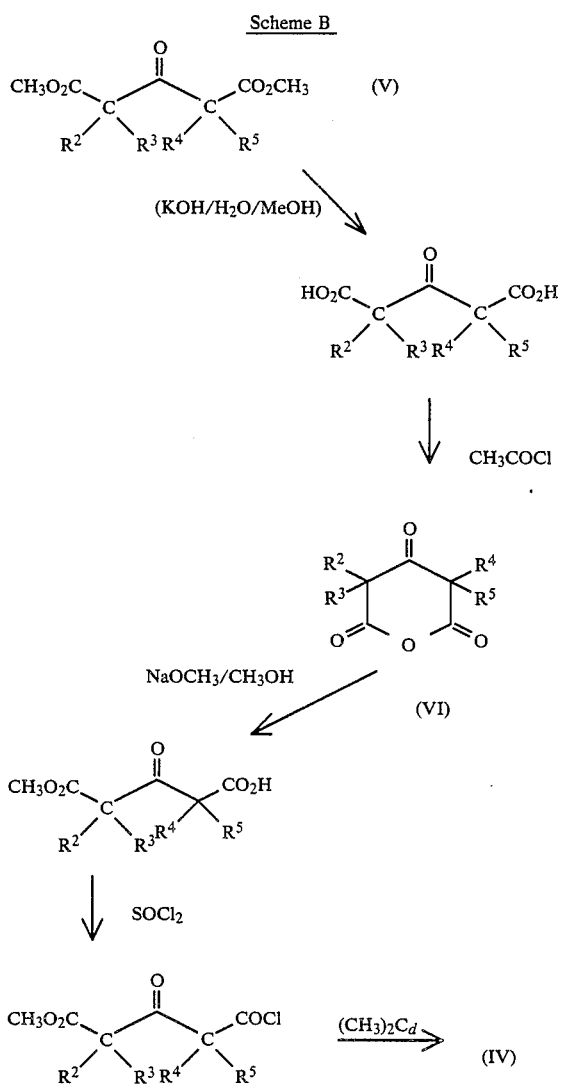

Precise reaction conditions for each step in Scheme B will depend upon the particular compounds involved and can be determined by routine procedures and the relevant literature.

Compounds of formula (V) can be prepared by the reaction of compounds of formula (VII):

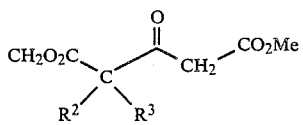

with a compound of formula $R^4X'$ and optionally thereafter with a compound of formula $R^5X'$ in the presence of a base such as sodium methoxide in an organic solvent such as methanol, wherein $R^4$, $R^5$ and $X'$ are as hereinbefore defined.

When $R^4$ and $R^5$ are the same, then the reaction can be carried out in a single step. By controlling the reaction conditions, the extent of the reaction (i.e. whether one or both hydrogen atoms on the methylene are replaced by $R^4$) can be determined.

Compounds of formula (VII) can be prepared by reaction of a compound of formula (VIII):

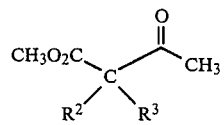

wherein $R^2$ and $R^3$ are as hereinbefore defined, with (a) a strong base such as lithium diisopropyl-amide and (b) $CH_3O_2CCl$ under conventional reaction conditions.

Compounds of formula (VIII) can be prepared by reaction a compound of formula (IX):

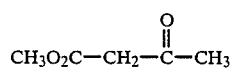

with a compound of formula $R^2X'$ in the presence of a base; and optionally thereafter $R^3X'$ wherein $R^2$, $R^3$ and $X'$ are hereinbefore defined, as described above for the reaction of the compound of formula (VII).

Alternatively in a further aspect of the invention compounds of formula (I) can be prepared by reacting a compound of formula (VI) as set out in Scheme B with a compound of formula (X):

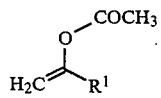

wherein $R^1$ is as hereinbefore defined, in the of a Lewis acid such as aluminium trichloride.

Reactions of this type are described by Merenyi and Nilson (Acta Chem. Scand, 1963, 17, 1801 and Acta Chem. Scand, 1964, 18, 1368).

Compounds of formula (X) are known compounds or they can be prepared from known compounds by conventional methods.

Furthermore, in yet another aspect of the invention compounds of formula (I) wherein $R^2$, $R^3$, $R^4$ and $R^5$ are the same, can also be prepared by reacting a compound of formula (XI):

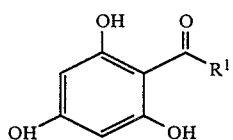

with a compound of formula $R^2X'$ in the presence of a base, wherein $R^1$, $R^2$ and $X'$ are as hereinbefore defined.

Suitable bases for use in the reaction are strong bases such as sodium methoxide The reaction is suitably carried out in an organic solvent such as methanol at temperatures of from 0° to 100° C.

When the compound of formula (I) contains a free hydroxy group, it may be derivatised to form salts, in particular agriculturally acceptable salts, acylates or sulphonates.

Suitable agriculturally acceptable salts include salts such as sodium, potassium, calcium and quaternary ammonium salts.

Suitable acylate derivatives are compounds wherein the OH moiety has been converted to a group of formula —OCOR$^6$ wherein R$^6$ is alkyl having for example from 1 to 6 carbon atoms, or aryl such as phenyl.

Suitable optionally substituted aryl groups R$^1$ include optionally substituted phenyl.

Suitable optional substituents for the group R$^1$ are up to three groups selected from halogen such as fluorine, chlorine and bromine; C$_{1-4}$ alkyl; C$_{1-4}$ alkoxy; halo (C$_{1-4}$) alkoxy such as trifluoromethoxy and tetrafluoroethoxy; cyano; nitro; C$_{1-4}$ haloalkyl such as trifluoromethyl; R$^7$SO$_n$— where n is 0, 1 r 2 and R$^7$ is C$_{1-4}$alkyl optionally substituted with halogen or cyano, phenyl or benzyl; NR$^8$R$^9$ wherein R$^8$ and R$^9$ are independently hydrogen or C$_{1-4}$ alkyl; R$^{10}$CO— where R$^{10}$ is C$_{1-4}$ alkyl or C$_{1-4}$ alkoxy; or SO$_2$NR$^8$R$^9$ where R$^8$ and R$^9$ are as defined above.

Preferred substituents for the group R$^1$ are one or two groups selected from halogen, haloalkyl in particular trifluoromethyl, R$^7$SO$_2$ such as MeSO$_2$—, nitro or cyano.

The group R$^1$ may, for example, contain one substituent in the ortho-position on the ring or it may contain substituents in both the ortho- and para-positions on the ring.

Preferably R$^1$ is substituted phenyl.

A suitable alkanoyl group for R$^2$, R$^3$, R$^4$ and R$^5$ is acetyl.

Preferably only one of R$^2$, R$^3$, R$^4$ and R$^5$ is either alkanoyl or —CO$_2$R$^a$.

Most preferably R$^2$, R$^3$, R$^4$ and R$^5$ are C$_{1-4}$ alkyl in particular methyl.

Examples of compounds of formula (I) are set out in Table I.

TABLE I

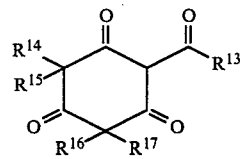

| COMPOUND NO. | R$^2$ | R$^3$ | R$^4$ | R$^5$ | R$^{11}$ | R$^{12}$ |
|---|---|---|---|---|---|---|
| 1 | CH$_3$ | CH$_3$ | CH$_3$ | CH$_3$ | Cl | H |
| 2 | CH$_3$ | CH$_3$ | CH$_3$ | CH$_3$ | Cl | Cl |
| 3 | CH$_3$ | CH$_3$ | CH$_3$ | CH$_3$ | Br | H |
| 4 | CH$_3$ | CH$_3$ | CH$_3$ | CH$_3$ | F | H |
| 5 | CH$_3$ | CH$_3$ | CH$_3$ | CH$_3$ | CF$_3$ | H |
| 6 | CH$_3$ | CH$_3$ | CH$_3$ | CH$_3$ | H | H |

Certain compounds of formula (I) are not described in European Patent Application No. EP-A-252298 and these form another aspect of the invention.

Yet further according to the invention there is provided a salt, acylate or sulphonate derivative of formula (I) or a compound of formula (IA)

(IA)

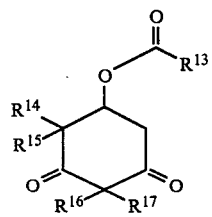

wherein R$^{13}$ is optionally substituted aryl and one or two groups R$^{14}$, R$^{15}$, R$^{16}$ and R$^{17}$ are C$_{1-4}$ alkanoyl or CO$_2$R$^9$ wherein R$^9$ is C$_{1-4}$ alkyl and the remainder are selected from hydrogen or C$_{1-4}$ alkyl; or R$^{13}$ is unsubstituted aryl and R$^{14}$, R$^{15}$, R$^{16}$ and R$^{17}$ are equivalent to R$^2$, R$^3$, R$^4$ and R$^5$ as hereinbefore respectively; and tautomers thereof.

Compound 6 herein is an example of a compound of formula (IA).

Compounds of formula (IA) can also be prepared by rearrangement of a compound of formula (XII):

(XII)

wherein R$^{13}$, R$^{14}$, R$^{15}$, R$^{16}$ and R$^{17}$ are as defined in relation to formula (IA) in the presence of a cyanide source and a moderate base.

The reaction is suitably carried out in an inert organic solvent such as acetonitrile and at a temperature of from −30° C. to 50° C., preferably at from 20° C.–40° C.

Suitable cyanide sources are alkali metal cyanides such as sodium and potassium cyanide; cyanohydrins of methyl alkyl ketones having from 1–4 carbon atoms in the alkyl groups, such as acetone or methyl isobutyl ketone cyanohydrins; cyanohydrins of benzaldehyde or of C$_2$–C$_5$ aliphatic aldehydes such as acetaldehyde, propionaldehyde, etc., cyanohydrins; zinc cyanide; tri(- lower alkyl) silyl cyanides, notably trimethyl silyl cyanide; and hydrogen cyanide itself.

A preferred cyanide source is acetone cyanohydrin.

The amount of the cyanide source employed is sufficient to catalyse the reaction, for example from 1–50 mole percent of the compound of formula (XII), preferably from 1 to 10 mole percent.

Suitable bases for use in the reaction are those described above for use in the reaction between the compound of formulae (II) and (III).

Suitably the base is used in an amount of from about 1 to about 4 moles per mole of compound of formula (II), preferably about 2 moles per mole.

Compounds of formula (XII) can be prepared by reacting a compound of formula (II) as hereinbefore defined with a compound of formula (XIII)

R$^{13}$COX    (XIII)

wherein R$^{13}$ is as defined in relation to formula (XII) and X is a leaving group in the presence of a base.

Suitable bases for use in the reaction are the moderate bases described above for use in the reaction of the compound of formula (II) with a compound of formula (III). A preferred base is triethylamine.

Suitable leaving groups X include halogen such as chlorine.

The reaction is suitably carried out in an inert organic solvent such as dichloromethane, methylene toluene, ethyl acetate or dimethylformamide at moderate temperatures of from 0° C. to 50° C., conveniently at room temperature.

Compounds of formula (XII) may also be prepared by reacting a compound of formula (II) with an acid of formula (XIV):

$$R^1CO_2H \qquad (XIV)$$

wherein $R^1$ is as defined in relation to formula (I), in the presence of a dehydrating agent and a basic organic catalyst.

Suitable dehydrating agents include dicyclohexylcarbodiimide (DCC) which is employed in an amount of at least one molar equivalent to the compounds of formulae (II) and (XIV).

Examples of suitable basic organic catalysts include 4-dimethylaminopyridine (DMAP) and 4-pyrrolidinopyridine (PPY).

The reaction is suitably carried out in an inert organic solvent such as acetonitrile, dichloromethane or 1,2-dichloroethane. Moderate temperatures for example from 0° C. to 40° C. can be employed, conveniently ambient temperature.

The salts, acylate or sulphonate derivatives of the compounds of formula (I) and compounds of formula (IA) are active as herbicides and therefore, in a further aspect the invention provides a process for severely damaging or killing unwanted plants which process comprises applying to the plants, or to the growth medium of the plants, an effective amount of a salt, acylate or sulphonate derivative of formula (I) or a compound of formula (IA) as hereinbefore defined.

These novel compounds are active against a broad range of weed species including monocotyledenous and dicotyledonous species. They may show some selectivity towards certain species.

The novel compounds may be applied directly to the plant (post-emergence application) or to the soil before the emergence of the plant (pre-emergence application). However, the compounds are, in general, more effective when applied to the plant pre-emergence.

The novel compounds of the invention may be used on their own to inhibit the growth of, severely damage, or kill plants but are preferably used in the form of a composition comprising a compound of the invention in admixture with a carrier comprising a solid or liquid diluent.

Therefore, in yet a further aspect the invention provides plant growth inhibiting, plant damaging, or plant killing compositions comprising a novel compound as hereinbefore defined and an inert carrier or diluent.

Compositions containing novel compounds of the invention include both dilute compositions, which are ready for immediate use, and concentrated compositions, which require to be diluted before use, usually with water. Preferably the compositions contain from 0.01% to 90% by weight of the active ingredient. Dilute compositions ready for use preferably contain from 0.01 to 2% of active ingredient, while concentrated compositions may contain from 20 to 90% of active ingredient, although from 20 to 70% is usually preferred.

The solid compositions may be in the form of granules, or dusting powders wherein the active ingredient is mixed with a finely divided solid diluent, e.g., kaolin, bentonite, kieselguhr, dolomite, calcium carbonate, talc, powdered magnesia, Fuller's earth and gypsum. They may also be in the form of dispersible powders or grains, comprising a wetting agent to facilitate the dispersion of the powder or grains in liquid. Solid compositions in the form of a powder may be applied as foliar dusts.

Liquid compositions may comprise a solution or dispersion of an active ingredient in water optionally containing a surface-active agent, or may comprise a solution or dispersion of an active ingredient in a water-immiscible organic solvent which is dispersed as droplets in water.

Surface-active agents may be of the cationic, anionic, or non-ionic type. The cationic agents are, for example, quaternary ammonium compounds (e.g. cetyltrimethylammonium bromide). Suitable anionic agents are soaps; salts or aliphatic mono ester of sulphuric acid, for example sodium lauryl sulphate; and salts of sulphonated aromatic compounds, for example sodium dodecylbenzenesulphonate, sodium, calcium, and ammonium lignosulphonate, butylnaphthalene sulphonate, and a mixutre of the sodium salts of diisopropyl and triisopropylnaphthalenesulphonic acid. Suitable non-ionic agents are the condensation products of ethylene oxide with fatty alcohols such as oleyl alcohol and cetyl alcohol, or with alkylphenols such as octyl- or nonyl-phenol or octyl-cresol. Other non-ionic agents are the partial esters derived from long chain fatty acids and hexitol anhydrides, for example sorbitan monolaurate; the condensation products of the partial ester with ethylene oxide; and the lecithins.

The aqueous solutions or dispersions may be prepared by dissolving the active ingredient in water or an organic solvent optionally containing wetting or dispersing agent(s) and then, when organic solvents are used, adding the mixture so obtained to water optionally containing wetting or dispersing agent(s). Suitable organic solvents include, for example, ethylene di-chloride, isopropyl alcohol, propylene glycol, diacetone alcohol, toluene, kerosene, methylnaphthalene, the xylenes and trichloroethylene.

The compositions for use in the form of aqueous solutions or dispersions are generally supplied in the form of a concentrate containing a high proportion of the active ingredient, and the concentrate is then diluted with water before use. The concentrates are usually required to withstand storage for prolonged periods and after such storage, to be capable of dilution with water to form aqueous preparations which remain homogeneous for a sufficient time to enable them to be applied by conventional spray equipment. Concentrates conveniently contain 20–90%, preferably 20–70%, by weight of the active ingredient(s). Dilute preparations ready for use may contain varying amounts of the active ingredient(s) depending upon the intended purpose; amounts of 0.01% to 10.0% and preferably 0.1% to 2%, by weight of active ingredient(s) are normally used.

A preferred form of concentrated composition comprising the active ingredient which has been finely divided and which has been dispersed in water in the presence of a surface-active agent and a suspending agent. Suitable suspending agents are hydrophilic colloids and include, for example, polyvinylpyrrolidone and sodium carboxymethylcellulose, and the vegetable gums, for example gum acacia and gum tragacanth. Preferred suspending agents are those which impart thixotropic properties too, and increase the viscosity of the concentrate. Examples of preferred suspending agents include hydrated colloidal mineral silicates, such as montmorillonite, beidellite, nontronite, hectorite, saponite, and saucorite. Bentonite is especially preferred. Other suspending agents include cellulose derivatives and polyvinyl alcohol.

The rate of application of the compounds of the invention will depend on a number of factors including, for example, the compound chosen for use, the identity of the plants whose growth is to be inhibited, the formulations selected for use and whether the compound is to be applied for foliage or root uptake. As a general guide, however, an application rate of from 0.005 to 20 kilograms per hectare is suitable while from 0.1 to 10 kilograms per hectare may be preferred.

The compositions of the invention may comprise, in addition to one or more compounds of the invention, one or more compounds not of the invention but which possess biological activity. Accordingly in yet a still further embodiment the invention provides a herbicidal composition comprising a mixture of at least one herbicidal compound of formula (I) as hereinbefore defined with at least one other herbicide.

The other herbicide may be any herbicide not having the formula (I) or (IA). It will generally be a herbicide having a complementary action in the particular application. For example it may be desirable in certain circumstances to use the novel compound of the invention in admixture with a contact herbicide.

Examples of useful complementary herbicides include:

A. benzo-2,1,3-thiadiazin-4-one-2,2-dioxides such as 3-isopropylbenzo-2,1,3-thiadiazin-4-one-2,2-dioxide (bentazon);
B. hormone herbicides, particularly the phenoxy alkanoic acids such as 4-chloro-2-methylphenoxy acetic acid (MCPA), 2-(2,4-dichlorophenoxy)propionic acid (dichlorprop), 2,4,5-trichlorophenoxyacetic acid (2,4,5-T), 4-(4-chloro-2-methylphenoxy)butyric acid (MCPB), 2,4-dichlorophenoxyacetic acid (2,4-D), 4-(2,4-dichlorophenoxy)butyric acid (2,4-DB), 2-(4-chloro-2-methylphenoxy)propionic acid (mecoprop), and their derivatives (eg. salts, esters and amides);
C. 3-[4-(4-halophenoxy)phenyl]-1,1-dialkylureas such as 3-[4-(4-chlorophenoxy)phenyl]-1,1-dimethylurea.
D. Dinitrophenols and their derivatives (e.g. acetates) such as 2-methyl-4,6-dinitrophenol (DNOC), 2-t-butyl-4,6-dinitrophenol (dinoterb), 2-secbutyl-4,6-dinitrophenol (dinoseb) and its ester, dinoseb acetate;
E. dinitroaniline herbicides such as N',N'-diethyl-2,6-dinitro-4-trifluoromethyl-m-phenylenediamine (dinitramine), 2,6-dinitro-N,N-dipropyl-4-trifluoromethylaniline (trifluralin) and 4-methylsulphonyl-2,6-dinitro-N,N-dipropylaniline (nitralin);
F. phenylurea herbicides such as N'-(3,4-dichlorophenyl)-N,N-dimethylurea (diuron) and N,N-dimethyl-N'-[3-(trifluoromethyl)phenyl]urea (flumeturon);
G. phenylcarbamoyloxyphenylcarbamates such as 3-[methoxy carbonylamino]phenyl (3-methylphenyl)-carbamate (phenmedipham) and 3-[ethoxycarbonylamino]phenyl phenylcarbamate (desmedipham);
H. 2-phenylpyridazin-3-ones such as 5-amino-4-chloro-2-phenylpyridazin-3-one (pyrazon);
I. uracil herbicides such as 3-cyclohexyl-5,6-trimethyleneuracil (lenacil), 5-bromo-3-sec-butyl-6-methyl-yl-uracil (bromacil) and 3-t-butyl-5-chloro-6-methyluracil (terbacil);
J. triazine herbicides such as 2-chloro-4-ethylamino-6-(i-propylamino)-1,3,5-triazine (atrazine), 2-chloro-4,6-di(ethylamino)-1,3,5-triazine (simazine) and 2-azido-4-(i-propylamino)-6-methylthio-1,3,5-triazine (aziprotryne);
K. 1-alkoxy-1-alkyl-3-phenylurea herbicides such as 3-(3,4-dichlorophenyl)-1-methoxy-1-methylurea (linuron), 3-(4-chlorophenyl)-1-methoxy-1-methylurea (monolinuron), 3-(4-bromo-4-chlorophenyl)-1-methoxy-1-methylurea (chlorobromuron).
L. thiolcarbamate herbicides such as S-propyl dipropylthiocarbamate (vernolate);
M. 1,2,4-triazin-5-one herbicides such as 4-amino-4,5-dihydro-3-methyl-6-phenyl-1,2,4-triazine-5-one (metamitron) and 4-amino-6-t-butyl-4,5-dihydro-3-methylthio-1,3,4-triazin-5-one (metribuzin);
N. benzoic acid herbicides such as 2,3,6-trichlorobenzoic acid (2,3,6-TBA), 3,6-dichloro-2-methoxybenzoic acid (dicamba) and 3-amino-2,5-diclorobenzoic acid (chloramben);
O. anilide herbicides such as N-butoxymethyl-chloro-2',6'-diethylacetanilide (butachlor), the corresponding N-methoxy compound (alachlor), the corresponding N-i-propyl compound (propachlor), 3',4'-dichloropropionanilide (propanil) and 2-chloro-N-[pyrazol-1-ylmethyl]acet-2'-6'-xylidide (metazachlor);
P. dihalobenzonitrile herbicides such as 2,6-dichlorobenzonitrile (dichlobenil), 3,5-dibromo-4-hydroxybenzonitrile (bromoxynil) and 3,5-diiodo-4-hydroxybenzonitrile (ioxynil);
Q. haloalkanoic herbicides such as 2,2-dichloropropionic acid (dalapon), trichloroacetic acid (TCA) and salts thereof;
R. diphenylether herbicides such as 4-nitrophenyl 2-nitro-4-trifluoromethylphenyl ether (fluorodifen), methyl 5-(2,4-dichlorophenoxy)-2-nitrobenzoate (bifenox), 2-nitro-5-(2-chloro-4-trifluoromethylphenoxy)benzoic acid (acifluorfen) and salts and ethoxy-4-nitrophenyl ether (oxyfluorfen) and 5-(2-chloro-4-(trifluoromethyl)phenoxy)-N-(methylsulfonyl)-2-nitrobenzamide (fomesafen): and
S. phenoxyphenoxypropionate herbicides such as 2-(4-(4'- trifluoromethylphenoxy)-phenoxy)-propionic acid methylester (trifop-methyl), 2-(4-((5-trifluoromethyl)-2-(pyridinyl)oxy)phenoxypropanoic acid (fluazifop) and esters thereof, 2-(4-((3-chloro-5-trifluoromethyl)-2-pyridinyl)oxy)phenoxy)propanoic acid (haloxyfop) and esters thereof, 2-(4-((6-chloro-2-quinoxalinyl)oxy)phenoxypropanoic acid (xylofop) and esters thereof; and
T. cyclohexanedione herbicides such as 2,2-dimethyl-4,6-dioxo-5-(1-((2-propenyloxy)amino)-butylidine) cyclohexane carboxylic acid (alloxydim) and salts thereof, 2-(1-ethoxyimino)butyl-5-(2-(ethylthio)-propyl)-3-hydroxy-2-cyclohexen-1-one (sethoxydim), 2-(1-(3-chloroallyloxyimino)butyl)-5-(2-ethylthiopropyl)-3-hydroxy cyclohex-2-enone (cloproxydim), 2-(1-ethoxyimino)butyl)-3-hydroxy-5-thian-3-yl cyclohex-2-enone (cycloxydim); and
U. sulfonyl urea herbicides such as 2-chloro-N-(4-methoxy-6-methyl-1,3,5-triazin-2-yl)-aminocarbonyl) benzenesulphonamide (chlorosulfuron), methyl 2-((((4,6-dimethyl-2-pyrimidinyl)amino)carbonyl)amino)sulphonyl)benzoic acid (sulfometuron), 2-(((3-(4-methoxy-6-methyl-1,3,5-triazin-2-yl)carbonyl- )amino)sulphonyl)benzoic acid (metsulfuron) and esters thereof;

V. imidazolidinone herbicides such as 2-(4,5-dihydro-4-isopropyl-4-methyl-5-oxoimidazol-2-yl)quinoline-3-carboxylic acid (imazaquin), methyl 6-(4-isopropyl-4-methyl-5-oxo-2-imidazolin-2-yl)-m-toluate and p-toluate isomer (AC 222293)

W. arylanilide herbicides such as 1-methylethyl-N-benzoyl-N-(3-chloro-4-fluorophenyl)-L-alanine (flamprop-isopropyl), ethyl N-benzoyl-N-(3,4-dichlorophenyl)-DL-alaninate (benzoylprop-ethyl), N-(2,4-difluorophenyl)-2-(3-(trifluoromethyl)-phenoxy)-3-pyridinecarboxamide (diflufenican): and X. amino acid herbicides such as N-(phosphonomethyl)glycine (glyphosate) and DL-homoalanin-4-yl(methyl)phosphinic acid (phosphinothricin) and their salts and esters; and Y. organoarsenical herbicides euch as monosodium methanearsonate (MSMA); and Z. miscellaneous herbicides including N,N-dimethyldiphenylacetamide (diphenamid), N-(1-naphthyl)phthalamic acid (naptalam) and 3-amino-1,2,4-triazole, 2-ethoxy-2,3-dihydro-3,3-dimethylbenzofuran methanesulfonate (ethofumesate), 1,4-epoxy-p-meth-2-yl 2-methylbenzyl ether (cinmethylin);

AA. Examples of useful contact herbicides include: bipyridylium herbicides such as those in which the active entity is the 1,1'-dimethyl-4,4'-dipyridylium ion (paraquat) and those in which the active entity is the 1,1'-ethylene-2,2'-dipyridylium ion (diquat);

The following examples illustrate the invention.

Preparation 1

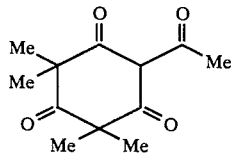

Iodomethane (17.04 g, 120 mmol) was added slowly to a solution of anhydrous 2,4,6-trihydroxyacetophenone (3.72 g, 20 mmol) and sodium methoxide (Na (2.76 g, 120 mmol) in MeOH (100 ml)). The reaction mixture was then heated under relux for 4 hours. Excess iodomethane and methanol were removed by concentration under reduced pressure to yield a yellow solid, which was dissolved in water and acidified with 2M hydrochloric acid (100 ml), whereupon a cream precipitate formed. The product was extracted with diethyl ether and the combined extracts washed with 20% w/v sodium sulphite solution. The aqueous sulphite washings were cautiously acidified with 2M hydrochloric acid to give a white precipitate, which was extracted with diethyl ether. All of the diethyl ether extracts were combined, dried over anhydrous magnesium sulphate, filtered and concentrated in vitro to give an orange oil which crystallised on standing to orange needles. Recrystallisation from 60°–80° C. bpt. petroleum ether afforded the tetra-methylated acetophenone (i) (3.22 g, 72%) as yellow needles, melting point 38°–40° C.

NMR (60 MHz, CDCl$_3$): δ 1.30 (6H, s), 1.39 (6H, s), 2.54 (3H, s), 18.18 (1H, s).

IR (nujol): 1720 (strong), 1670 (strong), 1560 (strong, broad) 1170 (medium) 1050 (strong) cm$^{-1}$.

Preparation 2

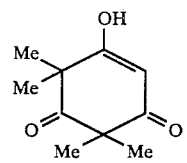

To the tetramethylated acetophenone (i) (2.91 g, 13.0 mmol) from Preparation 1 was added 2M hydrochloric acid (100 ml). The mixture was heated under reflux, whence enough ethanol was added to dissolve remaining solid. was continued for 32 hours, during which time concentrated hydrochloric acid (50 ml) was added portionwise. The solution was allowed to cool and the yellow plates formed were filtered off (1.33 g, 57%), point 184°–185° C.

NMR (60 MHz, CDCl$_3$): δ 1.7 (12H, s), 5.86 (1H, s). (enolic proton broad—not observed).

IR (nujol): 2550–2750 (broad), 1710 (strong), 1620 (strong), 1540 (strong), 1340 (weak), 1005 (strong), 1180 (strong), 1020 (medium) cm$^{-1}$.

m s.: M$^+$ 182.

Preparation 3

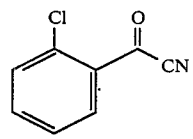

The reaction was carried out under Argon. Cuprous cyanide (5.0 g, 56 mmol) and anhydrous sodium iodide (15.6 g, 104 mmol) were stirred for 2 minutes with anhydrous acetonitrile (100 ml).

The resulting solution was mixed with o-chlorobenzoyl chloride (9.15 g, 52.3 mmol) whereupon an orange precipitate formed. The mixture was stirred for 30 minutes at room temperature, filtered and concentrated in vacuo. The residue was taken up in dichloromethane and the resulting precipitate was filtered off. Concentration in ave a yellow oil which crystallised on standing. Recrystallisation from 60°–80° C. b.p.t. petroleum ether gave o-chlorobenzoyl cyanide as white crystals (7.18 g 85%), melting point 33° C.

IR (nujol): 2200 (weak), 1680 (strong), 1580 (medium), 1230 (medium), 1070 (weak), 970 (weak), 780 (weak), 740 (medium).

g.c. m.s.: M$^+$ 165. ($^{35}$Cl).

EXAMPLE 1

This Example illustrates the preparation of Compound No. 1 in Table I.

The tetramethylated triketone (ii) (1.50 g, 8.24 mmol), prepared as described in Preparation 2, o-chlorobenzoyl cyanide (iii) (1.33 g, 8.24 mmol) prepared as described in Preparation 3, and anhydrous powdered zinc chloride (1.24 g, 9.06 mmol) were combined in dry acetonitrile (10 ml). Dry trietbylamine (1.37 ml, 9.89 mmol) in anhydrous acetonitrile (5 ml) was added dropwise to the mixture with cooling to −10° C. The reaction mixture was allowed to reach room temperature, then heated under reflux for 3 hours. The mixture was then poured into 2M hydrochloric acid (100 ml) and extracted with dichloromethane. The organic extracts were washed with 10% sodium carbonate solution (3×50 ml) and the aqueous Washings combined and acidified with 2M hydrochloric acid. The white precipitate was extracted with dichloromethane and concentrated in vacuo to give a yellow solid. Recrystallisation from a methanol water mixture afforded cream crystals (1.05 g, 40%), melting point 71°–72° C.

NMR (270 MHz, CDCl₃): δ 1.40 (6H, s), 1.60 (6H, s), 7.4–7.6 (4H, complex), 17.6 (1H, s).

IR (nujol) : 1720 (medium), 1680 (strong), 1560 (strong, broad), 1300 (medium), 1030 (medium).

m s.: MH+ 321. ($^{35}$Cl).

Preparation 4

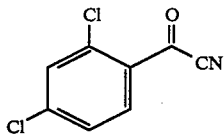
(iv)

The reaction was carried out under Argon. Cuprous cyanide (5.0 g, 56.0 mmol) and anhydrous sodium iodide (15.6 g, 104 mmol) were stirred for 2 minutes in anhydrous acetonitrile (100 ml). The resulting solution was mixed with 2,4-dichlorobenzoyl chloride (10.96 g, 52.3 mmol) whereupon an orange precipitate formed. The mixture was stirred for 30 minutes at room temperature, filtered and concentrated in vacuo. The residue was taken up in dichloromethane and the resulting precipitate was filtered off. Concentration of the filtrate under reduce pressure gave a yellow solid which was recrystallised from 60°–80° C. b.p.t. petroleum ether to give 2,4-dichlorobenzoyl cyanide as cream coloured crystals (8.36 g, 80%), melting point 73°–74° C.

NMR (60 MHz, CDCl₃): δ 7.5–8.1 (3H, complex).

IR (nujol): 220 (weak), 1680 (strong), 1580 (medium).

g.c. m.s.: M+ 199 ($^{35}$Cl).

EXAMPLE 2

This Example illustrates the preparation of Compound No. 2 in Table I.

The tetramethylated triketone (ii) (1.70 g, 9.34 mmol), 2,4-dichlorobenzoyl cyanide (iv) (1.84 g, 9.34 mmol) and anhydrous, powdered zinc chloride (1.4 g, 10.27 mmol) were combined in dry acetonitrile (10 ml). Triethylamine (1.56 ml, 11.21 mmol) in dry acetonitrile (5 ml) was added slowly to the mixture with cooling to −10° C. The reaction mixture was allowed to warm to room temperature, then heated under reflux for 3 hours. The mixture was then poured into 2M hydrochloric acid (100 ml) and extracted with dichloromethane. The organic extracts were washed with 10% sodium carbonate solution (3×50 ml) and the aqueous washings combined and acidified with 2M hydrochloric acid. The white precipitate was extracted with dichloromethane which was dried over magnesium sulphate, filtered and concentrated in vacuo to give orange crystals in an orange oil. Trituration with 60°–80° C. b.p.t. petroleum ether, filtration and concentration of the filtrate in vacuo gave a pale orange oil, which crystallised on standing to a yellow solid. Recrystallisation from an ethanol water mixture afforded cream crystals (0.75 g, 22.3%), melting point 61°–62° C.

NMR (270 MHz, CDCl₃): δ 1.36 (6H, s), 1.56 (6H, s), 7.2–7.4 (3H, complex), 17.4 (1H, s).

IR: 1720 (medium), 1680 (strong), 1560 (broad, strong), 1200 (weak), 1040 (weak) cm⁻¹.

m s.: M+ - Cl 319 ($^{35}$Cl).

Preparation 5

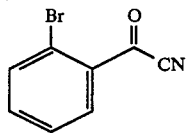
(v)

The reaction was carried out under Argon. Cuprous cyanide (6.52 g, 72.8 mmol) and anhydrous sodium iodide (20.25 g, 135 mmol) were stirred for 2 minutes in anhydrous acetonitrile (100 ml). The resulting solution was mixed with o-bromo benzoyl chloride (15.0 g, 68 mmol) whereupon an orange precipitate formed. The mixture was stirred for 30 minutes at room temperature, filtered and concentrated in vacuo. The residue was taken up in dichloromethane and the resulting precipitate was filtered off. Concentration of the filtrate under reduced pressure gave a yellow solid. Recrystallisation from 60°–80° C. b.p.t. petroleum ether afforded o-bromo benzoyl cyanide as yellow crystals (7.14 g, 50%), melting point 64° C.

IR (nujol): 2220 (weak), 1680 (strong), 1580 (medium) 1300 (medium), 1230 (strong), 980 (medium), 780 (medium), 730 (strong) cm⁻¹.

EXAMPLE 3

This Example illustrates the preparation of Compound No. 3 in Table I.

The tetramethylated triketone (ii) (1.19 g, 6.54 mmol), o-bromo.benzoyl cyanide (v) (1.37 g, 6.54 (mmol) and anhydrous, powdered zinc chloride (0.98 g, 7.19 mmol) were combined in dry acetonitrile (10 ml). Triethylamine (1.09 ml, 7.85 mmol) in dry acetonitrile (5 ml) was added slowly to the mixture with cooling to −10° C. The reaction mixture was allowed to warm to room temperature, then heated under reflux for 3 hours. The mixture was then poured into 2M hydrochloric acid (100 ml) and extracted with dichloromethane. The organic extracts were washed with 10% sodium carbonate solution (3×50 ml) and the carbonate washings were combined and acidified with 2M hydrochloric acid. The white precipitate was extracted with dichloromethane, dried over magnesium sulphate, filtered and concentrated in vacuo to give a cream solid. Recrystallisation from an ethanol water mixture gave a cream coloured crystalline solid (1.14 g, 48%), melting point 72°–73° C.

NMR (270 MHz, CDCl₃+d₆ DMSO): δ 1.35 (6H, s), 1.50 (6H, s), 7.2–7.6 (4H, complex) (enolic proton broad—not observed).

IR (nujol): 1720 (medium), 1680 (strong), 1560 (strong, broad), 1300 (medium, broad), 1200 (weak), 1020 (medium), 770 (medium) cm⁻¹.

m.s.: M+ - Br 285.

Preparation 6

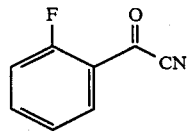
(vi)

The reaction was carried out under Argon. Cuprous cyanide (4.67 g, 52.2 mmol) and anhydrous sodium iodide (14.61 g, 97 mmol) were stirred for 2 minutes in anhydrous acetonitrile (100 ml). The resulting solution was mixed with o-fluoro benzoyl chloride (7.73 g, 48.7 mmol) whereupon an orange precipitate formed. The mixture was stirred for 30 minutes at room temperature, filtered and concentrated in vacuo. The residue was taken up in dichloromethane and the resultant precipitate was filtered off.

Concentration of the filtrate under reduced pressure gave an orange oil. Distillation in Kugelrör apparatus gave o-fluorobenzoyl cyanide as a yellow liquid (5.07 g, 66%).

NMR (60 MHz, CDCl$_3$): δ 7.2–8.2 (4H, complex).
IR (liquid film): 2225 (medium), 1680 (strong), 1610 (strong), 1580 (medium), 750 (strong) cm$^{-1}$.
g.c. m .s.: M$^+$ 149.

EXAMPLE 4

This Example illustrates the preparation of Compound No. 4 in Table I.

The tetramethylated triketone (ii) (1.19 g, 6.54 mmol), o-fluorobenzoyl cyanide (vi) (0.97 g, 6.54 mmol) and anhydrous zinc chloride (0.98 g, 7.19 mmol) were combined in dry acetonitrile (10 ml). Triethylamine (1.09 ml, 7.85 mmol) in acetonitrile (5 ml) was added slowly to the mixture with cooling to $-10°$ C. The reaction was stirred at this temperature for 2 hours, then allowed to warm to room temperature. After standing for 16 hours the reaction mixture was poured into 2M hydrochloric acid (100 ml) and extracted with dichloromethane. The organic extracts were washed with 10% sodium carbonate solution (3×50 ml) and the aqueous washings combined and carefully acidified to give a white solid which was filtered off. This was purified on a column of silica using the solvent system hexane, ether and acetic acid in a raio of 50:50:2. Concentration in vacuo of the first component to come off the column afforded an orange solid, which was recrystallised from a methanol water mixture to give yellow crystals (0.7 g, 35%) melting point 69°–70° C.

NMR (90 MHz, CDCl$_3$): δ 1.4 (6H, s), 1.56 (6H, s), 6.9–7.6 (5H, complex), 17.4 (1H, s).
IR (nujol): 3500 (medium, 1720 (weak), 1680 (strong), 1620 (weak), 1560 (medium, broad), 1220 (weak), 760 (medium) cm$^{-1}$.
m.e.: M$^+$ 304.

Preparation 7

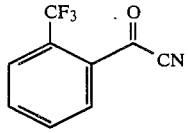
(vii)

The reaction was carried out under Argon. Cuprous cyanide (4.22 g, 47 mmol) and anhydrous sodium iodide (13.12 g, 87 mmol) were stirred for 2 minutes in anhydrous acetonitrile (100 ml). The resulting solution was mixed with o-trifluoromethylbenzoyl chloride (9.16 g, 44 mmol) whereupon an orange precipitate formed. The reaction mixture was stirred for 30 minutes at room temperature, filtered and concentrated in vacuo. The residue was taken up in dichloromethane and the resultant precipitate was filtered off. Concentration of the filtrate in vacuo gave an orange oil which crystallised on standing.

Recrystallisation from 60°–80° C. b.p.t. petroleum ether gave a o-fluoromethylbenzoyl cyanide as pale yellow crystals (3.5 g, 40%), melting point 41° C.

NMR (60 MHz, CDCl$_3$): δ 7.27–8.37 (4H, complex).
IR (nujol): 2225 (weak), 1700 (strong), 1600 (weak), 1580 (medium), 970 (strong) cm$^{-1}$.
g.c. m.s.: M$^+$ 199.

EXAMPLE 5

This Example illustrates the preparation of Compound No. 5 in Table I.

The tetramethylated triketone (ii) (1.13 g, 6.21 mmol), o-trifluoromethylbenzol cyanide (vi) (1.23 g, 6.21 mmol) and anhydrous powdered zinc chloride (0.93 g, 6.83 mmol) were combined in dry acetonitrile (10 ml). Triethylamine (1.03 ml, 7.45 mmol) in dry acetonitrile (5 ml) was added slowly to the mixture with cooling to $-10°$ C. The reaction mixture was then allowed to reach room temperature then heated under reflux for 4 hours. The reaction mixture was poured into 2M hydrochloric acid (100 ml) and extracted with dichloromethane. The organic extracts were washed with 10% sodium carbonate solution (3×50 ml) and the aqueous washings combined and acidified to give a white precipitate. Extraction with dichloromethane, drying over magnesium sulphate, filtration and concentration in vacuo gave an oily orange solid. Trituration with 60°–80° C. b.p.t. petroleum ether, filtration and concentration of the filtrate in vacuo gave a yellow oil which was purified on a column of silica using the solvent system hexane, ether and acetic acid in the ratio 50:50:5. Concentration in vacuo of the first fraction to come off the column gave a yellow oil (0.60 g, 27%).

NMR (400 MHz, CDCl$_3$): δ 1.3 (6H, s), 1.55 (6H, s), 7.2–7.9 (4H, complex) (enolic proton broad—not observed).
IR (liquid film): 1725 (medium, 1680 (strong), 1560 (strong, broad), 1320 (strong), 760 (strong).
m.s.: M$^+$ 354.

EXAMPLE 7

This Example illustrates the preparation of compound 6 in Table 1.

Sodium (2.76 g, 0.12 mol) was added to methanol (200 ml) slowly with stirring. Phlorobenzophenone (4.6 g, 0.02 mol) was stirred into the solution then methyliodide (17.4 g, 0.12 mol) was added slowly and the reaction mixture heated under reflux for 4 hours. Excess methyl iodide and methanol were removed by concentration in vacuo to give a yellow solid, which was dissolved in water, acidified with 2M HCl and extracted with ether. The ethereal phase was washed with sodium sulphite and the sodium sulphite washings were then acidified with 2M HCl and taken up in ether. The combined ether extracts were washed with water, dried over MgSO$_4$ and concentrated in vacuo to give oily orange needles, which were recrystallised from ethanol/water to give pale yellow needles, 3.0 g, 53% mpt. 71°–72° C.

ir (Nujol) 1725, 1680, 1600, 1280, 1160, 1040, 860, 840, 770 cm$^{-1}$.

Biological Data

The herbicidal activity of compound 6 was tested as follows:

The compound in the appropriate concentration was incorporated into a 4% emulsion of methyl cyclohexanone and a 0.4% blend of 3.6 parts Tween 20 and 1 part Span 80. Tween 20 is a Trade Mark for a surface active agent comprising a condensate of 20 molar proportions of ethylene oxide with sorbitan laurate. Span 80 is a Trade Mark for a surface-active agent comprising sorbitan monoalaurate. Formulation was effected by dissolving the compound in the requisite amount of solvent/surfactant blend. If necessary glass beads were added, the total liquid volume adjusted to 5 ml with water and the mixture shaken to effect complete dissolution of the compound. The formulation so prepared, after removal of beads were necessary, was then diluted to final spray volume (45 ml) with water).

The spray compositions so prepared were sprayed onto young pot plants (post-emergence test) at a rate equivalent to 1000 liters per hectare. Damage to plants was assessed 13 days after spraying by comparison with untreated plants, on a scale of 0 to 5 where 0 is 0–10% damage, 1 is 11 to 25% damage, 2 is 26–50% damage, 3 is 51–80% damage, 4 is 81–95% damage and 5 is 96–100% damage.

In a test carried out to detect pre-emergence herbicidal activity, seeds of the test species were placed on the surface of plastic trays of compost and sprayed with the compositions at the rate of 1000 liters per hectare. The seeds were then covered with further compost. 20 Days after spraying, the seedlings in the sprayed plastic trays were compared with the seedlings in unsprayed control trays, the damage being assessed on the same scale of 0 to 5.

The results of the tests are given in Table II below.

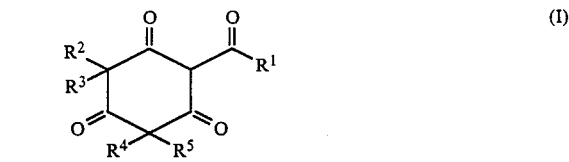

or a salt, acylate or sulphonate derivative thereof; wherein $R^1$ is an optionally substituted aryl group where the optional substitution is up to three groups selected from halogen; $C_{1-4}$ alkyl; $C_{1-4}$ alkoxy; halo $(C_{1-4})$ alkoxy; cyano; nitro; $C_{1-4}$ haloalkyl; $R^7SO_n$— where n is 0, 1 or 2 and $R^7$ is $C_{1-4}$ alkyl or $C_{1-4}$ alkyl substituted with halogen or cyano, phenyl or benzyl; $NR^8R^9$ where $R^8$ an $R^9$ are independently hydrogen or $C_{1-4}$ alkyl $R^{10}CO$— where $R^{10}$ is $C_{1-4}$ alkyl or $C_{1-4}$ alkoxy; or $SO_2NR^8R^9$ where $R^8$ and $R^9$ are as defined above, $R^2$, $R^3$, $R^4$, and $R^5$ are selected from hydrogen, $C_{1-4}$ alkyl, $C_{1-4}$ alkanoyl or —$CO_2R^a$ wherein $R^a$ is $C_{1-4}$ alkyl or $R^2$ and $R^3$ or $R^4$ and $R^5$ together with the carbon atom to which they are attached form a $C_{3-6}$ cycloalkyl ring, provided that at least $R^2$ and $R^3$ or $R^4$ and $R^5$ are not both hydrogen and that not more than two of $R^2$, $R^3$, $R^4$ and $R^5$ are $C_{1-4}$ alkanoyl or —$CO_2R^a$; which process comprises reacting a compound of formula (II)

TABLE II

| COMPOUND NO. | RATE OF APPLICATION kg/ha | PRE- OR POST-EMERGENCE APPLICATION | PLANTS (see Table III) | | | | | | | | | | | |
|---|---|---|---|---|---|---|---|---|---|---|---|---|---|---|
| | | | Sb | Rp | Ct | Sy | Mz | Ww | Rc | Bd | Ip | Am | Pi | Ca |
| 6 | 4 | Pre | 5 | 4 | 1 | 2 | 0 | 0 | 0 | 2 | 1 | 0 | 0 | 4 |
| | | Post | 3 | 4 | 0 | 3 | 3 | 3 | 3 | 2 | 3 | 1 | 2 | 3 |

| COMPOUND NO. | RATE OF APPLICATION kg/ha | PRE- OR POST-EMERGENCE APPLICATION | TEST PLANTS (see Table III) | | | | | | | | | | | |
|---|---|---|---|---|---|---|---|---|---|---|---|---|---|---|
| | | | Ga | Xa | Ab | Co | Av | Dg | Al | St | Ec | Sh | Ag | Cn |
| 6 | 4 | Pre | 0 | 0 | 5 | 2 | 0 | 4 | 0 | 3 | 3 | 4 | 0 | 3 |
| | | Post | 2 | 2 | 4 | 0 | 2 | 4 | 0 | 3 | 3 | 1 | 2 | 3 |

Abbreviations used for Test Plants
Sb - Sugar beet
Rp - Rape
Ct - Cotton
Sy - Soybean
Mz - Maize
Ww - Winter wheat
Rc - Rice
Bd - *Bidens pilosa*
Ip - *Ipomoea purpurea*
Am - *Amarunthus retroflexus*
Pi - *Polygonum aviculare*
Ca - *Chenopodium album*
Ga - *Galium aparine*
Xa - *Xanthium spinsum*
Xs - *Xanthium strumarium*
Ab - *Abutilon theophrasti*
Co - *Cassia obtusifolia*
Av - *Avena fatua*
Dg - *Digitaria sanguinalis*
Al - *Alopercurus myosuroides*
St - *Setaria viridio*
Ec - *Echinchloa crus-galli*
Sh - *Sorghum halepense*
Ag - *Agropyron repens*
Cn - *Cypenus rotundus*

I claim:
1. A process for preparing a compound of formula (I) which comprises wherein $R^2$, $R^3$, $R^4$ and $R^5$ are as defined in relation to formula (I) with a compound of formula (III):

$$R^1COCN \quad \text{(III)}$$

wherein $R^1$ is as defined in relation to formula (I) in the presence of a base and a Lewis acid; and thereafter if desired forming a salt, or sulphonate derivative.

2. A process according to claim 1 for the preparation of a compound of formula (I) wherein $R^1$ is an optionally substituted phenyl group.

3. A process according to claim 1 or claim 2 wherein the group $R^1$ contains a substituent in the ortho position.

4. A process according to claim 3 wherein the compound of formula (I) contains an additional substituent at the para position.

5. A process according to any one of the preceding claims wherein $R^1$ is optionally substituted by up to three groups selected from halogen such as fluorine, chlorine and bromine; $C_{1-4}$ alkyl; $C_{1-4}$ alkoxy; halo $(C_{1-4})$ alkoxy such as trifluoromethoxy and tetrafluoroethoxy; cyano; nitro; $C_{1-4}$ haloalkyl such as trifluoromethyl; $R^7SO_n-$ where n is 0, 1 or 2 and $R^7$ is $C_{1-4}$ alkyl optionally substituted with halogen or cyano, phenyl or benzyl; $NR^8R^9$ wherein $R^8$ and $R^9$ are independently hydrogen or $C_{1-4}$ alkyl; $R^{10}CO-$ where $R^{10}$ is $C_{1-4}$ alkyl or $C_{1-4}$ alkoxy; or $SO_2NR^8R^9$ where $R^8$ and $R^9$ are as defined above.

6. A process according to any one of the preceding claims wherein $R^2$, $R^3$, $R^4$ and $R^5$ are $C_{1-4}$ alkyl, in particular methyl.

7. A process according to claim 1 wherein the solvent is a dry aprotic solvent.

8. A process according to claim 1 wherein the base is a tertiary amine or alkali metal carbonate or phosphate; the Lewis acid is zinc chloride or aluminum trichloride; the solvent is acetonitrile or methylene chloride; and the reaction temperature is $-20°$ C. to $+90°$ C.; and the salt is an agriculturally acceptable sodium, potassium, calcium, or quaternary ammonium salt or an acylate of the formula $-OCOR^6$ where $R^6$ is alkyl of 1 to 6 carbons or phenyl.

* * * * *